United States Patent [19]

Takami et al.

[11] 4,415,877

[45] Nov. 15, 1983

[54] GAS SENSING ELEMENT

[75] Inventors: Akio Takami; Tsutomu Saito; Toshifumi Sekiya; Hideki Kudo, all of Nagoya, Japan

[73] Assignee: NGK Spark Plug Co., Ltd., Aichi, Japan

[21] Appl. No.: 371,343

[22] Filed: Apr. 23, 1982

[30] Foreign Application Priority Data

Apr. 25, 1981 [JP] Japan .................................. 56/63175

[51] Int. Cl.³ ............................................. H01L 7/00
[52] U.S. Cl. ................................. 338/34; 174/126 CP; 338/322
[58] Field of Search ..................... 338/34, 35, 25, 28, 338/322, 324; 174/126 CP; 219/541; 73/27 R; 422/98; 428/670, 607, 620

[56] References Cited

U.S. PATENT DOCUMENTS

| 3,432,278 | 3/1969 | Richards | 428/670 |
| 3,443,914 | 5/1969 | Hayashi | 428/670 X |
| 3,457,539 | 7/1969 | Lupfer | 428/670 X |
| 4,053,864 | 10/1977 | Rodriguez et al. | 338/322 X |
| 4,249,156 | 2/1981 | Micheli | 73/27 R X |

Primary Examiner—C. L. Albritton
Attorney, Agent, or Firm—Sughrue, Mion, Zinn, Macpeak & Seas

[57] ABSTRACT

A gas sensing element having an oxide semiconductor element is provided with lead wires partially embedded therein. The lead wires are formed of a nickel core and a cover layer of at least 5μ in thickness and made of platinum or platinum alloy containing from 1 to 10 percent low catalytic metal.

7 Claims, 1 Drawing Figure

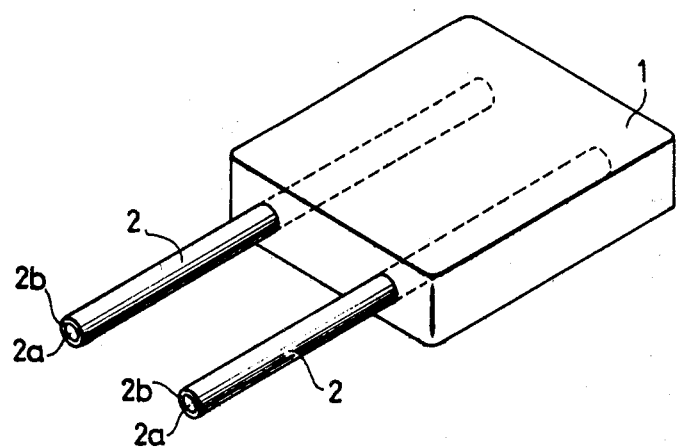

GAS SENSING ELEMENT

BACKGROUND OF THE INVENTION

This invention relates to a gas sensing element using a semiconductor made of sintered metal oxide, for detecting the partial pressure of oxygen gas in an gas atmosphere from a variation in the electrical resistance of the semiconductor.

The conventional gas sensing element includes a semiconductor made of a sintered oxide of a metal such as titanium dioxide cobalt, tin or chromium, and a pair of electrodes embedded in the semiconductor, as lead wires across the electrical resistance of the semiconductor. This gas sensing element has been extensively employed as a gas component detecting device to control the exhaust gas of a combustion machine, such as an internal combustion engine, to decrease emission.

To form a gas sensing element of this type, a pair of electrodes are embedded in a mass of metal oxide powder, which is the raw material of the semiconductor. The electrodes and the mass of metal oxide powder are molded in a die under pressure and are then subjected to sintering at a temperature of 1200° C. or higher. Therefore, even if sintering is carried out in an inert atmosphere, the electrodes are unavoidably oxidized. Accordingly, the electrodes are made of expensive platinum or a platinum alloy such as platinum-rhodium (hereinafter referred to as "platinum metal"), to prevent oxidation. On the other hand, the semiconductor made of the sintered oxide (hereinafter referred to as "an oxide semiconductor") is made porous to increase the gas sensing ability. Therefore, CO and HC in the exhaust gas enter the porous semiconductor and come in contact with the platinum metal electrodes, and carbon is deposited by their catalytic reaction. This carbon accumulates on the electrodes, causes stress on the oxide semiconductor, expanding the latter, and occasionally destructive failure are occurred. In this point, the conventional gas sensing element is disadvantageous.

SUMMARY OF THE INVENTION

An object of this invention is to eliminate the above-described drawback accompanying a conventional gas sensing element. A feature of the gas sensing element according to the invention resides in that nickel wires, covered to a thickness of at least 5μ with an alloy of essentially platinum metal and a low catalytic metal, are employed as a pair of electrodes embedded in the oxide semiconductor, for leading out the electrical resistance of the oxide semiconductor.

BRIEF DESCRIPTION OF THE DRAWINGS

The single FIGURE in the accompanying drawing is a perspective view of a gas sensing element according to this invention.

DETAILED DESCRIPTION OF THE PREFERRED EMBODIMENTS

Examples of catalytic metals which may be used in the invention are gold, silver, nickel, cobalt, iron, titanium and copper. The nickel wires are covered with an alloy essentially of platinum metal and one or more of these low catalytic metals in a range of from 1 to 10% by weight. As a result, the electrodes are not oxidized when heated together with the oxide semiconductor, and deposition of carbon during the catalytic reaction is prevented, although the electrodes come in contact with CO and HC gases during the operation.

A cover layer may be formed on the nickel wire with the platinum metal alloy according to conventional methods such as metallurgical clad chemical plating, vacuum evaporation, sputtering, and metallizing methods. However, in view of work efficiency, metallurgical clad, the chemical plating method and the vacuum evaporation methods are more suitable. It is desirable that the cover layer be a clad layer, because it is uniform in thickness and no pin holes are created therein. Since the cover layer must be sufficiently high in dictility and flexibility in rolling and withdrawing a clad wire, the low catalytic metal to be mixed with the platinum metal is selected from a group of metals such as gold, nickel, cobalt and iron which will create no intermetallic compound with the platinum metal.

In the invention, the content of the low catalytic metal is limited to 1 to 10% with respect to that of the platinum metal because if the content of the low catalytic metal is less than 1%, the effect is considerably low, and if it exceeds 10%, the electrodes are broken when used for a long time.

The reason why the electrodes are broken is estimated to be as follows:

When the electrodes are heated for a long time during operation, an intermetallic compound is formed between the low catalytic metal and the platinum metal, as a result of which the cover layer is embrittled. Furthermore, the thermal expansion coefficient of the cover layer made of the platinum metal alloy is about $9 \times 10^{-6}$, while that of the nickel wire is much higher, about $14 \times 10^{-6}$. Accordingly, the cover layer thus embrittled cannot follow the thermal expansion of the nickel wire, and finally it is cracked, which results in the breakage of the electrode.

The cover layer should be as thin as possible because the thickness of the cover layer does not directly concern its durability. In the case where the cover layer is formed by chemical plating, vacuum evaporation, or sputtering as was described before, it should have a thickness of at least 5μ, because in this case no pin holes are formed therein, which increases the acid resistance when the cover layer is sintered together with the oxide semiconductor. The clad cover layer should also have a thickness of at least 5μ in view of the convenience of manufacture. It is desirable for both cover layers to have a thickness of about 50μ in view of both manufacturing cost and stability.

EXAMPLE

A pair of electrodes 2 were embedded in an oxide semiconductor 1 to a depth of 1 mm, with 2.5 mm being exposed, and were spaced by 1.2 mm from each other, to fabricate a gas sensing element. The oxide semiconductor 1 was of titanium dioxide and had a porosity of about 30%. After being sintered, the oxide semiconductor 1 was 2 mm in thickness, 2.5 mm in width and 3.5 mm in length and had slightly rounded corners. Each electrode 2 was prepared by forming a cover layer 2b of 50μ in thickness by cladding an alloy containing essentially platinum metal and low catalytic metal, on the surface of a nickel wire 2a of 0.35 mm diameter.

The electrodes 2 of the gas sensing element 1 thus fabricated were inserted into a pair of insulating tubes (not shown), each being 50 mm in length and having an inside diameter of 0.9 mm, and were sealed with heatresisting cement (not shown). The insulating tubes were secured to the exhaust pipe of a four-cylinder 1800 cc. car engine in such a manner that the gas sensing element was set at the center of the exhaust pipe. Under this condition, an electrode endurance test was carried out under full load. The test results detected at time intervals of 50 hours are as indicated in the following Table. It should be noted that a number of electrodes were prepared using different materials, and three specimens of each electrode were subjected to the endurance test. Therefore, each endurance test result is represented by the shortest time required for carbon deposition and the shortest time required for electrode breakage in the Table.

both cases. The electrode indicated by specimen numbers 21 through 27 whose cover layers were formed with alloy containing less than 1% low catalytic metal by weight, deposited carbon in 100 hours which might result in the semiconductor cracks. On the other hand, in specimen numbers 61 through 66 in which the content of low catalytic metal was more than 10%, no carbon was deposited, but electrodes were broken in 50 to 150 hours due to brittle properties of the intermetallic compound.

The above-described Table has been prepared by using electrodes which were fabricated by convering the nickel wires with alloys which contain platinum and low catalytic metal, by cladding. The cover layers may

TABLE

| SPECIMEN NO. | COVER LAYER COMPOSITION | | | ENDURANCE TEST RESULTS ELECTRODE | | REMARKS |
|---|---|---|---|---|---|---|
| | PLATINUM METAL | LOW CATALYTIC METAL | | CARBON DEPOSITION TIME (Hr) | BREAKAGE TIME (Hr) | |
| 1 | Pt | — | | 50 | 200 | REFERENCE |
| 2 | 87Pt—13Rh | — | | 100 | At least 400 | OUT OF |
| 21 | Pt 99.5 | Au | 0.5 | 100 | At least 400 | THE RANGE |
| 22 | | Ni | " | " | " | |
| 23 | | Co | " | " | " | |
| 24 | | Fe | " | " | " | |
| 25 | | Ag | " | " | " | |
| 26 | | Ti | " | " | " | |
| 27 | | Cu | " | " | " | |
| 31 | Pt 99.0 | Au | 1 | 250 | At least 400 | WITHIN |
| 32 | | Ni | " | " | " | THE RANGE |
| 33 | | Co | " | 200 | " | |
| 34 | | Fe | " | " | " | |
| 35 | | Ag | " | " | " | |
| 36 | | Ti | " | " | " | |
| 37 | | Cu | " | " | " | |
| 41 | Pt 95.0 | Au | 5.0 | At least 400 | At least 400 | WITHIN |
| 42 | | Ni | " | " | " | THE RANGE |
| 43 | | Co | " | " | " | |
| 44 | 87Pt—13Rh | Au | " | " | " | |
| 45 | Total:95.0 | Ni | " | " | " | |
| 46 | | Co | " | " | " | |
| 47 | | Ti | " | " | " | |
| 51 | Pt 90.0 | Au | 10.0 | At least 400 | 200 | WITHIN |
| 52 | | Ni | " | " | " | THE RANGE |
| 53 | | Co | " | " | " | |
| 54 | | Fe | " | " | " | |
| 55 | | Ag | " | " | " | |
| 56 | | Ti | " | " | " | |
| 57 | | Cu | " | " | " | |
| 61 | Pt 85.0 | Au | 15.0 | At least 400 | 100 | WITHIN |
| 62 | | Ni | " | " | 150 | THE RANGE |
| 63 | | Co | " | " | 100 | |
| 64 | | Fe | " | " | " | |
| 65 | | Ag | " | " | 50 | |
| 66 | | Ti | " | " | " | |
| 67 | | Cu | " | " | " | |

As is apparent from the above-described Table, the electrodes indicated by specimen numbers 31 through 37, 41 through 47 and 51 through 57 whose cover layers were formed with platinum metals which contained 1 to 10% low catalytic metals, Au, Ni, Co, Fe, Ag, Ti and Cu by weight showed no abnormal results after a 200 hour endurance test, and especially ones with Au, Ni, Co and Ti contained therein provided significantly satisfactory results. On the other hand, the electrodes whose cover layers were formed with platinum metal typically platinum or platinum-rhodium, which did not contain the above-described low catalytic metal, deposited carbon in fifty to one hundred hours. In the case of platinum, the electrode was broken in 200 hours; and in the case of platinum-rhodium, the electrode was broken in 400 hours. It can be estimated that the electrode breakage was due to the accumulation of carbon, in be formed by chemical plating or vacuum evaporation, as described above. For instance, in the case of an electrode fabricated under the same conditions as those described except that the cover layer, similarly as in specimen number 41, containing 95% platinum and 5% gold, was formed by chemical plating, no carbon was deposited in 400 hours. The endurance test result ws the same as that of specimen number 41.

Two or more low catalytic metals may be contained in platinum metal. In the case of an electrode which was fabricated under the same conditions as those described above except that a cover layer of an alloy consisting of 2.5% gold and 2.5% nickel as low catalytic metals and 95% platinum was formed by cladding, no carbon was deposited in 400 hours. Similarly to electrodes indicated by specimen numbers 41 and 42, the endurance test results of the electrode thus fabricated were much better than those of the electrode indicated by specimen numbers 21 through 27 and 61 through 67, and those of the electrodes indicated by specimen numbers 1 and 2 which had cover layers of platinum or platinum-rhodium only (including no low catalytic metal); however, the effect of employing two or more kinds of low catalytic metals was not significant.

As was described above, the gas sensing element according to the invention includes the semiconductor prepared by sintering a metal oxide and one pair of electrodes which are fabricated by coating the surface of two nickel wires with an alloy which contains platinum metal and one or two low catalytic metals in a range of from 1 to 10% by weight, the electrodes being embedded in the semiconductor. Accordingly, with the gas sensing element of the invention, the consumption of expensive platinum metal is greatly reduced when compared with that of the conventional gas sensing element in which the platinum metal wires are employed as electrodes. Furthermore, as is apparent from the example described above, the endurance has been remarkably improved according to the invention.

What is claimed is:

1. A gas sensing element, comprising:
   a semiconductor formed of a sintered metal oxide and having an electrical resistance varying with a gas component to be sensed;
   a pair of lead electrodes embedded in said semiconductor, each of said electrodes comprising a nickel wire core and a cover layer surrounding said core, said cover layer comprising an alloy essentially containing platinum metal and including at least one low catalytic metal in a range of from 1 to 10% by weight.

2. A gas sensing element as claimed in claim 1, wherein said low catalytic metal is selected from the group consisting of gold, nickel, cobalt, iron, silver, titanium and copper.

3. A gas sensing element as claimed in claim 1, wherein said cover layer is a clad layer.

4. A gas sensing element as claimed in claim 3, wherein in said clad cover layer said low catalytic metal is selected from the group of gold, nickel, cobalt and iron.

5. A gas sensing element as claimed in claim 1, said cover layer being a vapor evaporated layer.

6. A gas sensing element as claimed in claim 1, said cover layer being a plated layer.

7. A gas sensing element as claimed in claim 1, said cover layer having a thickness of at least $5\mu$.

* * * * *